(12) United States Patent
Thomas et al.

(10) Patent No.: US 8,791,060 B2
(45) Date of Patent: *Jul. 29, 2014

(54) COMPOSITION AND USE OF PHYTO-PERCOLATE FOR TREATMENT OF DISEASE

(75) Inventors: Tiffany Thomas, Scottsdale, AZ (US); Michael Tempesta, El Granada, CA (US)

(73) Assignee: Health Enhancement Products, Inc., Bloomfield Hills, MI (US)

( * ) Notice: Subject to any disclaimer, the term of this patent is extended or adjusted under 35 U.S.C. 154(b) by 670 days.

This patent is subject to a terminal disclaimer.

(21) Appl. No.: 12/897,574

(22) Filed: Oct. 4, 2010

(65) Prior Publication Data
US 2011/0081319 A1    Apr. 7, 2011

Related U.S. Application Data

(63) Continuation of application No. 11/606,676, filed on Nov. 30, 2006, now Pat. No. 7,807,622, and a continuation-in-part of application No. PCT/US2006/015302, filed on Apr. 20, 2006, said application No. 11/606,676 is a continuation-in-part of application No. PCT/US2005/013375, filed on Apr. 20, 2005.

(60) Provisional application No. 60/565,011, filed on Apr. 23, 2004, provisional application No. 60/719,025, filed on Sep. 21, 2005, provisional application No. 60/741,774, filed on Dec. 2, 2005.

(51) Int. Cl.
*C07K 14/00* (2006.01)
*A61K 36/02* (2006.01)
*A61K 31/715* (2006.01)
*A61K 38/16* (2006.01)

(52) U.S. Cl.
CPC .................. *A61K 38/16* (2013.01); *A61K 36/02* (2013.01); *A61K 31/715* (2013.01)
USPC .............................................. 514/1; 530/350

(58) Field of Classification Search
USPC .............................................. 514/1; 530/350
See application file for complete search history.

(56) References Cited

U.S. PATENT DOCUMENTS

| 9,479 | A | 12/1852 | Atkins |
|---|---|---|---|
| 10,480 | A | 1/1854 | Page |
| 152,587 | A | 6/1874 | Woodside |
| 4,822,612 | A | 4/1989 | Shinpo |
| 6,461,607 | B1 | 10/2002 | Farmer |
| 6,551,596 | B2 | 4/2003 | Kralovec |
| 6,673,908 | B1 | 1/2004 | Stanton |
| 6,733,751 | B2 | 5/2004 | Farmer |
| 7,125,846 | B2 | 10/2006 | Rojkjaer |
| 7,807,622 | B2 | 10/2010 | Thomas et al. |
| 2002/0009479 | A1 | 1/2002 | Vardi et al. |
| 2002/0119164 | A1 | 8/2002 | Uchiyama et al. |
| 2005/0114920 | A1 | 5/2005 | Yusibov et al. |
| 2007/0207231 | A1 | 9/2007 | Thomas et al. |

FOREIGN PATENT DOCUMENTS

| JP | 0409040523 A | 2/1997 |
|---|---|---|
| WO | 03028749 A1 | 4/2003 |
| WO | WO2005/112987 A2 | 1/2005 |
| WO | 2005112987 | 12/2005 |
| WO | WO2006/113925 | 10/2006 |
| WO | WO2007/065024 | 6/2007 |

OTHER PUBLICATIONS

Kim et al. Purification and characterization of a fibrinolytic enzyme produced from *Bacillus* sp. strain CK 11-4 screened from Chungkook-Jang. Appl. Environ. Microbiology, Jul. 1996, vol. 62, No. 7, pp. 2482-2488, p. 2482, In 4: abstract.
www.optimumchoices.com/spirulina.htm (2007).
www.michaelkiriac.com (Jan. 1, 2003).
www.nlm.nih.gov/medlineplus/druginfo/natural/patient-spirulina. html (Aug. 1, 2006).
Communication pursuant to Article 94(e) EPC dated Nov. 20, 2009 for International Patent Application No. 06758513.3-2043.
Article entitled "Lipids in Health and disease: The effects of ProAlgaZyme novel algae infusion on metabolic syndrome and markers of cardiovascular health," by Julius Oben, Ebangha Enonchong, Dieudonne Kuate, Dora Mbanya, Tiffany C Thomas, DeWall J Hildreth, Thomas D Ingolia and Michael S. Tempesta. Published in BioMed Central, Sep. 5, 2007, p. 1-9.
Press Release entitled "Western Glory Hole Inc. Enters Definitive Agreement with Health Enhancement Products Inc." dated Oct. 30, 2003, Business Wire.
Office Action for International Patent Application No. 06838974.1 dated Feb. 23, 2010.
Abstract entitled "A water-soluble antitumor glycoprotein from *Chlorella vulgaris*," by Noda K, Ohno N, Tanaka K, Karniya N, Okuda M, Yadornae T, Nomoto K, Shoyama Y. Department of Pharmacognosy, Faculty of Pharmaceutical Sciences, Kyushu University, Fukuoka, Japan, dated Oct. 1996. PubMed.
Written Opinion of the International Searching Authority dated Dec. 6, 2005 for International Patent Application No. PCT/US05/13375.
International Preliminary Report on Patentability dated Oct. 25, 2006 for International Patent Application No. PCT/US05/013375.
Written Opinion of the International Searching Authority dated Mar. 22, 2007 for International Patent Application No. PCT/US06/15302.
International Preliminary Report on Patentability dated Oct. 23, 2007 for International Patent Application No. PCT/US2006/015302.
International Search Report dated Jun. 4, 2008 for International Patent Application No. PCT/US06/46320.
Final Office Action dated Nov. 3, 2008 for U.S. Appl. No. 11/587,266.

(Continued)

*Primary Examiner* — Karen Cochrane Carlson
(74) *Attorney, Agent, or Firm* — Snell & Wilmer L.L.P.

(57) ABSTRACT

This invention relates generally to a method of preparation of a phyto-percolate that is derived from fresh water mixture including algae. The phyto-percolate is believed to contain an enzyme having proteolytic activity. The invention further relates to the use of the phyto-percolate in a variety of disease state.

13 Claims, 4 Drawing Sheets

(56) References Cited

OTHER PUBLICATIONS

Nonfinal Office Action dated Feb. 4, 2008 for U.S. Appl. No. 11/587,266.
Spirulina. (2010). MedlinePlus. U.S. National Library of Medicine and the National Institutes of Health. Retrieved Apr. 14, 2010 from http://www.nlm.nih.gov/medlineplus/druginfo/natural/patient-spirulina.html as accessed Apr. 14, 2010.
BioSuperfood-Algae/Spirulina for People. (2010). Optimum Choices. Retrieved Apr. 14, 2010 from http://www.optimumchoices.com/spirulina.htm as accessed Apr. 14, 2010.
Search Report for European Patent Application No. 06758513 dated Sep. 24, 2009.
Nonfinal Office Action dated Oct. 19, 2010 for U.S. Appl. No. 12/067,735.
Article entitled "Using Chemopreventive Agents to Enhance the Efficacy of Cancer Therapy" by Fazlul H. Sarkar and Yiwei Li, Published in Cancer Res 2006; 66: (7). Apr. 1, 2006, pp. 3347-3350.
Office Action dated Dec. 20, 2012 in U.S. Appl. No. 12/947,684.
International Search Report for Patent Application No. PCT/US2010/056862 dated Jul. 29, 2011.
International Search Report for Patent Application No. PCT/US2011/025713 dated Jun. 21, 2011.
Article entitled "Arteriosclerosis, Thrombosis, and Vascular Biology: Regulation of Plasma High-Density Lipoprotein Levels by the ABCA1 Transporter and the Emerging Role of High-Density Lipoprotein in the Treatment of Cardiovascular Disease," by H. Bryan Brewer, Jr. Alan T. Remaley, Edward B. Neufeld, Federica Basso and Charles Joyce. Published by the American Heart Association, originally published online Aug. 19, 2004.
Australian Examiner's Report for Patent Application No. PCT/US2006/046320 dated Aug. 25, 2011.
Office Action dated Sep. 9, 2011 for U.S. Appl. No. 12/947,684.
Office Action for U.S. Appl. No. 12/067,735 dated Jul. 20, 2011.
Office Action Summary dated Mar. 13, 2012 for U.S. Appl. No. 12/067,735.
Office Action dated Oct. 22, 2012 in U.S. Appl. No. 12/067,735.
Scientific Paper Pub. Jun. 2012 in the Journal of Nutrition and Dietary Supplements by Smiti Gupta and group at WSU.
Australian Patent Examination Report dated Sep. 7, 2012.
EPO Communication re: European Patent Application No. 10830908.9 dated Mar. 7, 2012.
EPO Communication re: European Patent Application No. 06758513.3 dated Mar. 22, 2012.
Office Action dated May 21, 2012 for U.S. Appl. No. 12/947,684.
Office Action dated May 24, 2013 in Canadian Patent Application No. 2,631,773.
Office Action dated Aug. 7, 2012 in Japanese Patent Application No. 2008543545.
Notice of Allowance dated May 13, 2013 in U.S. Appl. No. 12/067,735.
"Research Indicates ProAlgaZyme may Decrease Risk of Stroke or Heart Attack," Jan. 20, 2004, retrieved online: http://www.supplementquality.com/efficacy/ProAlgaZyme.html.
Office Action dated Oct. 9, 2013 for U.S. Appl. No. 12/947,684.

COMPOSITION AND USE OF PHYTO-PERCOLATE FOR TREATMENT OF DISEASE

CROSS-REFERENCE TO RELATED APPLICATIONS

This patent application is a continuation application of and claims priority to U.S. patent application Ser. No. 11/606,676 filed on Nov. 30, 2006 entitled "Composition and Use of Phyto-Percolate for Treatment of Disease," which claims the benefit of priority to U.S. Provisional Application No. 60/741,774 filed on Dec. 7, 2005. The '676 application is also a continuation-in-part of International Application No. PCT/US06/15302 filed on Apr. 20, 2006 entitled "Composition and Use of Phyto-Percolate for Treatment of Disease," which claims the benefit of U.S. Provisional Application Nos. 60/741,774 filed Dec. 2, 2005 and 61/719,025 filed on Sep. 21, 2005. The '676 is also a continuation-in-part of International Application No. PCT/US05/13375 entitled "Method and Preparation of Use of Fibrinolytic Enzymes in the Treatment of Disease," which claims the benefit of U.S. Provisional Patent Application Ser. No. 60/565,011, filed on Apr. 23, 2004. The contents of all of these related applications are incorporated herein by reference in their entirety.

FIELD OF INVENTION

This invention relates generally to methods and compositions for treating human diseases, disorders, and conditions using a preparation of a phyto-percolate isolated from a complex mixture of fresh water algae and other microorganisms.

BACKGROUND OF THE INVENTION

Enzymes have a very important use within biochemical cycles in the human body. The majority of acute and chronic diseases create an inflammatory process that results in the destruction of surrounding tissue. This tissue debris becomes toxic and further hinders the processes of detoxification, elimination and defense by way of free radical oxidation. Proteolytic enzymes are responsible for the body's detoxification processes. As humans age and chronic disease processes progress, a deficiency of the proteolytic enzymes that carry out the body's waste detoxification processes may be experienced. This enzymatic deficiency aids in the production of a chronic hyper-inflammatory state, and the disease process becomes much more complex.

Enzymes are the catalysts that control and direct all metabolic processes. Without adequate enzymes in the body, chaos reigns and the immune system and other metabolic processes become less efficient, making tissue repair slow and poorly replicated. Proteolytic enzymes, or proteases, are enzymes capable of breaking down proteins by cleaving peptide bonds. They are produced and utilized by every living organism on Earth for protection, nutrient breakdown and assimilation, and waste removal. Many degenerative diseases stem from proteolytic enzyme deficiencies, leading to the inadequate removal of carcinogenic wastes from the body.

It is believed that the immune system, which helps protect us from diseases including cancer, cardiovascular disease, and other immune deficient or deregulated disorders, can become ineffective because of advanced disease state or age. Immune deficiency caused by disease state or advancing age can impair benefits received from the use of therapeutic drugs that may be taken for the treatment of these various disorders. Therapeutic drugs may lose their effectiveness in a compromised immune system as a disease state progresses due to metabolic dysfunction or poor therapeutic drug assimilation.

With advancing age, humans experience an increasing accumulation of environmental influences that are believed to have toxic effects on the human body. An observed effect associated with aging is a less accurate tissue repair process, possibly an expression of DNA mutations caused by environmental factors. Because of these alterations, foreign antigens in the way of microbes, and environmental toxins such as radiation and chemical compounds through foods, water, and air, are allowed to increasingly invade the human organism. These environmental toxins are introduced primarily through the mucous membranes of the intestinal tract, upper respiratory tracts and lungs.

Human genes, which are made up of double-strands of DNA, are the directors of tissue repair. It is believed that through advancing age and contact with the surrounding destructive elements, the expression of such DNA may become less and less accurate because of replication errors and mutations, thus creating very different functional end products of repair when compared to a younger individual.

Impaired immune protection and regulation, it is believed, allows an increasing amount of toxic environmental components to invade the cells of our bodies. These toxic components express destructive patterns of oxidation by way of free radical activity, thus rendering important metabolic processes to function inadequately. Because of biochemical cellular destruction, dead, fractionated cellular components are created, adding to the toxic manifestations. White cells, which are an important part of the immune system, congregate at the sites of tissue destruction in an effort to slow the process down. A chemical reaction that takes place at the site causes inflammation that further increases the destructive pattern. This pattern of tissue destruction, secondary to foreign antigen invasion and the associated white cell activity, can create an ongoing autoimmune hyperactive inflammatory state and an increasing amount of toxic tissue destruction and debris. Because of the increased inefficiency of tissue repair and the ever presence of surrounding environmental influences, human metabolic processes become less and less efficient with age.

The inner lining of the blood vessels, particularly the arteries, can be affected by this destructive pattern. Because many environmental contaminants are introduced into human bodies through the intestinal tract and lungs, they spread through the body by way of the vascular bed, thus coming first in contact with the inner lining of the blood vessels. This ongoing contact in the inner lining of the arteries with toxic free radicals results in the destructive oxidative process. This maintains an ongoing inflammatory state that includes cell break down and scar tissue formation in the form of sclerotic plaques. These plaques are made up of fibrous tissue, cholesterol, calcium deposits and necrotic tissue (broken down cellular components). Increasing arterial restriction and blood thickening due to pathological fibrin diminishes blood flow and alters oxygen and nutrient distribution to vital organs. This gradually increasing cellular starvation affects the functions of the brain, heart, kidneys, muscles, joints and other vital systems.

It is believed that accelerated DNA mutations and errors in replication, increased oxidation, inflammation, dysregulated white cell activity, and tissue destruction are the results of a gradual progression of contact with environmental forces, including pathogenic microbials. The amount of contact depends on lifestyle and individual health care. Some illnesses either originate from excessive free radical oxidation destruction at the body's cellular level, or cause a great increase in free radical oxidation destruction. Therefore, when the body's own metabolic and healing processes are unable to cope with the excess of toxic waste products, a cycle of ongoing inflammation and disease is created that interferes with the body's normal immune activity and tissue repair. Tissue destruction also activates the body's coagulation, or blood-clotting, mechanism, generating a barrage of intravascular thrombi, or blood clots, and blood-thickening fibrin, that can precipitate strokes, heart attacks, pulmonary emboli, kidney damage, and phlebitis.

Oxidative free radical activity becomes rampant because of the action of the involving white cells attempting to control the initial cause of the destruction. The resulting pathological agents secondary to this influence of white cell activity create an ongoing destructive pattern upon local surrounding tissue, the endothelial cells that line the vascular bed, and the epithelial cells lining the intestinal tract. Not only is there destructive activity upon the above-mentioned tissues but also there is oxidative breakdown or pathological activation of the coagulation factors. This includes pathologically activated fibrinogen to produce a soluble fibrin that, unlike insoluble fibrin, which is an important component of the normal blood-clotting mechanism, cannot be cross-linked and is pathological, or harmful to the body. This soluble fibrin not only negatively influences general capillary circulation but also kidney filtration, oxygen exchange within the alveoli of the lungs, and oxygenation of brain tissue. It not only thickens the blood, but is in itself an oxidative free radical, and contributes to the degenerative oxidation process.

Much of the expressed symptomatology from the production of soluble fibrin is caused by gram-negative bacteria, mycoplasma and *Candida albicans*, which are allowed to flourish in the immune-compromised environment created by excess wastes and fibrin, and is related to the cellular destruction and by-products of ongoing free radical activity. Fibrinolytic activity, or the process of breaking down fibrin, along with the eradication of the foreign pathological agents by other therapeutic interventions, can lead to increasingly effective immune system and white cell activity, and will greatly accelerate the healing process.

Most cancer processes liberate hydrogen peroxide, which acts as a free radical oxidative agent. In addition to hydrogen peroxide, the effects of cancer growth and chemotherapy produce excess soluble fibrin products as a response to these abnormal and destructive processes. The fibrin is produced as part of the body's natural reaction to tissue damage, which also occurs normally at the site of a superficial wound. However, at the site of cancer growth, fibrin coats cancer cells, tragically insulating them from destruction by the body's immune system. These coagulation mechanisms, stimulated by the oxidative damage associated with chronic illness, the damaging effects of chemotherapy, and the nature of abnormal cancer growth, all lead to further damage. Chronic illnesses such as cancer produce an acceleration of disseminated intravascular coagulation, causing not only a build-up of soluble fibrin but also of small intravascular thrombi, or clots that float around the vascular bed acting as emboli that obstruct circulation. The use of a fibrinolytic agent, along with any other therapeutic regime, will increase immune regulation and the effectiveness of white cell activity, improve capillary circulation and nutrient flow to the body's organs, aid in eliminating toxins, and enhance the benefits of other therapeutic agents. In addition, fibrinolytic agents will reduce the amount of free radical soluble fibrin that accelerates degenerative oxidation, and can increase the body's immune effectiveness in combating cancer growth.

In vivo laboratory monitoring of disease processes has supported the observations that improved cellular function and efficiency come with less oxidative, free radical activity, improved cellular nutrition, enhanced immune activity and white cell function and improved oxygenation.

SUMMARY OF THE INVENTION

In one aspect, the invention provides a method for treating or preventing a disorder in a mammal (e.g., human, dog, cat, horse, etc.) by administering to the mammal a therapeutically effective amount of phyto-percolate or derivative thereof.

In useful embodiments, the phyto-percolate derivative is a protein having a molecular weight of about 67.5 kDa, a protein having a molecular weight of about 21.0 kDa, or a polysaccharide. In another embodiment, the phyto-percolate derivative has fibrinolytic enzymatic activity. The phyto-percolate derivative may be isolated from the phyto-percolate or it may be produced by any appropriate method known in the art. Suitable methods for producing the phyto-percolate derivative include, for example, recombinantly expressing the derivative (e.g., protein) by a microorganism and synthetically producing a derivative (i.e., chemical (cell-free) synthesis). The recombinant microorganism may be one or more of the species present in ATCC Deposit #PTA-5863, or it may be any other appropriate specie.

In particular embodiments a particular dosage is between about 1 and about 8 ounces per day of the phyto-percolate. Particularly noted is a dosage of about 1 to about 4 ounces per day. Preferably, the phyto-percolate that is administered to the human contains between about 10 ppm and about 150 ppm of a phyto-percolate derivative. In another useful embodiment, a therapeutically effective amount of one or more of the derivatives is administered to the human. Preferably, the mammal is administered between about 1 mg and 1000 mg of the derivative per day. Suitable methods for administration of the phyto-percolate include oral administration. Suitable methods for administration of a phyto-percolate derivative (e.g., an isolated derivative) include, for example, oral, topical, rectal, or vaginal administration as well as intravenous, intramuscular, and subcutaneous injection.

Another aspect of this invention is directed to a method of treating an overweight condition or obesity comprising administering to the mammal (e.g., human) a therapeutically effective amount of a phyto-percolate or derivative thereof.

Another aspect of this invention is directed to a method for treating type I and II diabetes comprising administering to the mammal (e.g., human) a therapeutically effective amount of a phyto-percolate or derivative thereof.

Another aspect of this invention is directed to a method for treating an inflammatory disorder comprising administering to the mammal (e.g., human) a therapeutically effective amount of a phyto-percolate or derivative thereof. It is believed that the phyto-percolate and derivatives have broad spectrum anti-inflammatory properties and therefore may be used to reduce or prevent inflammation in a wide range of diseases and disorders.

Another aspect of this invention is directed to a method for treating a stomach disorder comprising administering to the mammal (e.g., human) a therapeutically effective amount of a phyto-percolate or derivative thereof. Stomach disorders amenable to treatment with the phyto-percolate and/or derivatives thereof include, for example, a stomach ulcer and gastric reflux disease.

In another aspect of this invention, the phyto-percolate or derivatives may be used to alleviate side-effects of another primary therapy. For example, the phyto-percolate may be administered to reduce the oxidative stress, chemotherapy-induced nausea, chemotherapy-induced liver damage, appetite suppression, hair loss, fingernail and toenail loss and discoloration that result from anti-AIDS therapy and anticancer therapy (e.g., chemotherapy and radiation therapy).

In another aspect of this invention, the phyto-percolate or derivatives may be used to reduce the recovery time in mammals (e.g., humans and horses) after periods of stress (e.g., exercise). In a related aspect, the phyto-percolate or derivatives are administered in order to restore physical energy and mental acuity following periods of stress.

In another aspect of this invention, the phyto-percolate or derivates may also be administered topically directly to the eye (e.g., in the form of eye drops) to treat lesions of the cornea, dry eyes, and similar ocular disorders.

Another aspect of this invention is directed to a method for treating conditions or disorders associated with infectious disease (e.g., a viral infection) comprising administering to the mammal (e.g., human) a therapeutically effective amount of a phytopercolate or derivative thereof. Infectious disease may be the cause of many of the above and below listed diseases such as pneumonia, all viruses, acariosis, acne, adenovirus, AIDS, amebiasis, anthrax, athlete's food, babesiosis, bartonellosis, Bell's palsy, botulism, candidiasis, carbuncles, Chaga's disease, chicken pox, Chlamydia, coccidiomycosis, coronavirus, cryptococcosis, cytomegalovirus, Dengue fever, echovirus, erysipelas, furuncle, gangrene, Guillan-Barre syndrome, hepatitis, impetigo, influenza, leucopenia, Lyme's disease, malaria, martolditis, measles, mumps, mycobacterium, mycosis, parasites, pediculosis, P.I.D. pyodermia, rabies, rubella, salmonella, salpingitis, septicemia, shingles, sinusitis, syphilis, tetanus, Tindi Cruzi and warts.

Another aspect of this invention is directed to a method for treating diseases related to the heart, blood vessels, renal, liver, and endocrine system comprising administering a therapeutically effective amount of a phyto-percolate or derivative thereof.

Another aspect of this invention is directed to a method for treating a vasospasm comprising administering to a mammal (e.g., human) a therapeutically effective amount of a phyto-percolate or derivative thereof.

Another aspect of this invention is directed to a method for treating heart failure comprising administering to a mammal (e.g., human) a therapeutically effective amount of a phyto-percolate or derivative thereof.

Another aspect of this invention is directed to a method for treating cardiac hypertrophy comprising administering to a mammal (e.g., human) a therapeutically effective amount of a phyto-percolate or derivative thereof.

Another aspect of this invention is directed to a method for treating dysregulated blood pressure comprising administering to a mammal (e.g., human) a therapeutically effective amount of a phyto-percolate or derivative thereof.

Another aspect of this invention is directed to a method for treating angina comprising administering to a mammal (e.g., human) a therapeutically effective amount of a phyto-percolate or derivative thereof.

Another aspect of this invention is directed to a method for treating peripheral vascular disease comprising administering to a mammal (e.g., human) a therapeutically effective amount of a phyto-percolate or derivative thereof.

Another aspect of this invention is directed to a method for treating cerebral diseases and diseases related to the central nervous system that are vascular in origin comprising administering to a mammal (e.g., human) a therapeutically effective amount of a phytopercolate or derivative thereof.

Another aspect of this invention is directed to a method for treating neurodegeneration comprising administering to a mammal (e.g., human) a therapeutically effective amount of a phyto-percolate or derivative thereof.

Another aspect of this invention is directed to a method for treating Alzheimer's disease comprising administering to a mammal (e.g., human) a therapeutically effective amount of a compound of a phyto-percolate or derivative thereof.

Another aspect of this invention is directed to a method for treating depression comprising administering to a mammal (e.g., human) a therapeutically effective amount of a phyto-percolate or derivative thereof.

Another aspect of this invention is directed to a method for treating addiction, including drug detoxification and/or substance abuse including nicotine, cocaine and alcohol abuse comprising administering to a mammal (e.g., human) a therapeutically effective amount of a phyto-percolate or derivative thereof.

Another aspect of this invention is directed to a method for treating attention deficit disorder and attention deficit hyperactivity disorder comprising administering to a mammal (e.g., human) a therapeutically effective amount of a compound of a phyto-percolate or derivative thereof.

Another aspect of this invention is directed to a method for treating sleep disorders comprising administering to a mammal (e.g., human) a therapeutically effective amount of a phyto-percolate or derivative thereof.

Another aspect of this invention is directed to a method for treating seasonal affective disorder comprising administering to a mammal (e.g., human) a therapeutically effective amount of a phyto-percolate or derivative thereof.

Another aspect of this invention is directed to a method for treating environmental and food allergies comprising administering to a mammal (e.g., human) a therapeutically effective amount of a phyto-percolate or derivative thereof.

Another aspect of this invention is directed to a method for treating conditions related to pain or nocioception comprising administering to a mammal (e.g., human) a therapeutically effective amount of a phyto-percolate or derivative thereof.

Another aspect of this invention is directed to a method for treating migraine comprising administering to a mammal (e.g., human) a therapeutically effective amount of a compound of a phyto-percolate or derivative thereof.

Another aspect of this invention is directed to a method for treating disorders related to disruption of circadian rhythms including jet lag comprising administering to a mammal (e.g., human) a therapeutically effective amount of a phyto-percolate or derivative thereof.

Another aspect of this invention is directed to a method for treating diseases related to abnormal gastrointestinal motility, secretion, and/or function comprising administering to a mammal (e.g., human) a therapeutically effective amount of a phyto-percolate or derivative thereof.

Another aspect of this invention is directed to a method for treating diarrhea and/or incontinence comprising administering to a mammal (e.g., human) a therapeutically effective amount of a phyto-percolate or derivative thereof.

Another aspect of this invention is directed to a method for treating a gastric ulcer comprising administering to a mammal (e.g., human) a therapeutically effective amount of a phyto-percolate or derivative thereof.

Another aspect of this invention is directed to a method for treating irritable bowel syndrome comprising administering to a mammal (e.g., human) a therapeutically effective amount of a phyto-percolate or derivative thereof.

Another aspect of this invention is directed to a method for treating inflammatory bowel disease comprising administering to a mammal (e.g., human) a therapeutically effective amount of a phyto-percolate or derivative thereof.

Another aspect of this invention is directed to a method for treating nausea comprising administering to a mammal (e.g., human) a therapeutically effective amount of a phyto-percolate or derivative thereof.

Another aspect of this invention is directed to a method for treating sexual dysfunction comprising administering to a mammal (e.g., human) a therapeutically effective amount of a phyto-percolate or derivative thereof.

Another aspect of this invention is directed to a method for altering fertility comprising administering to a mammal (e.g., human) a therapeutically effective amount of a phyto-percolate or derivative thereof.

Another aspect of this invention is directed to a method for treating conditions or disorders associated with the immune system comprising administering to a mammal (e.g., human) a therapeutically effective amount of a phyto-percolate. Immune system deficiency may be the cause of many of the above and below listed diseases such as cancer, emphysema, encephalitis, environmental sensitivity, erysipelas, food poisoning and Reynaud's disease.

Another aspect of this invention is directed to a method for treating conditions or disorders associated with hormonal imbalances comprising administering to a mammal (e.g., human) a therapeutically effective amount of a phyto-percolate. Hormonal imbalances may be the cause of many of the above and below listed diseases such as acne, Addison's disease, endometriosis, Grave's disease, osteoporosis, menstrual and menopausal regulation, glucose, and other metabolic regulation. In this regards, the phyto-percolate and derivatives may be used to improve the general health and overall function of metabolic organs like the kidney, liver, and pancreas. It is believed that the phyto-percolate and derivatives improve the efficiency of those organs and increases their metabolic and endocrine functions.

Another aspect of this invention is directed to a method for treating conditions or disorders associated with neurological deficiencies comprising administering to a mammal (e.g., human) a therapeutically effective amount of a phyto-percolate. Neurological deficiencies may be the cause of many of the above and below listed diseases such as Lou Gehrig's disease, chronic pain, Huntingdon's Chorea, diabetic neuropathy, multiple sclerosis, Myasthenia Gravis, Parkinson's disease, poliomyelitis, senile dementia, nigrostriatal degeneration, stroke, tardive dyskinesia and tinnitus.

Another aspect of this invention is directed to a method for treating respiratory diseases comprising administering to a mammal (e.g., human) a therapeutically effective amount of a phyto-percolate.

Another aspect of this invention is directed to a method for treating asthma comprising administering to a mammal (e.g., human) a therapeutically effective amount of a phyto-percolate.

Another aspect of this invention is directed to a method for treating diseases related to abnormal hormone release and utilization comprising administering to a mammal (e.g., human) a therapeutically effective amount of a phyto-percolate.

Another aspect of this invention is directed to a method for treating abnormal insulin release and utilization comprising administering to a mammal (e.g., human) a therapeutically effective amount of a compound of a phyto-percolate.

Another aspect of this invention is directed to a method for treating skin lesions and disorders.

In addition to the "direct" effect of the phyto-percolate of this invention there are diseases/conditions wherein subjects with said diseases/conditions will benefit from the associated weight loss, and metabolic and immune system regulation, such as insulin resistance with impaired glucose tolerance, Type II Diabetes, hypertension, hyperlipidemia, cardiovascular disease, gall stones, certain cancers, sleep apnea, etc. resulting from use of phyto-percolate.

In a further illustrative embodiment a method of making the inventive phytopercolate is disclosed. The phyto-percolate is prepared by cultivating a mixture of freshwater algae and bacteria that is augmented by a nutrient blend that is related to the production of fibrinolytic enzymes, proteins, and other molecules, forming a fortified algae culture. Added to this fortified algal and bacterial culture is purified fresh water that has been purified by reverse osmosis, distillation and/or deionization. The culture is percolated with said purified fresh water and nutrient blend for a predetermined time forming a phytopercolate. The phyto-percolate is decanted from the fortified algal and bacterial culture and processed. Suitable methods of processing the phyto-percolate include filtration, centrifugation, lyophilization, purification, dilution, and other methods. The filtering of the decanted phyto-percolate in one particular embodiment is by micro-filtration where the micro-filtration removes particles larger than about 0.22 µm.

In another aspect, this invention provides a substantially pure compound isolated from a phyto-percolate. In a preferred embodiment, the compound is isolated from the percolate produced by culturing the microorganisms of ATCC Deposit #PTA-5863 or other appropriate species as described herein. In another embodiment, the compound is a protein having a molecular weight of about 67.5 kDa.

In a related aspect, the invention provides a pharmaceutical formulation comprising a substantially pure compound isolated from a phyto-percolate and a pharmaceutically acceptable excipient.

The term "inflammatory disorder" encompasses a variety of conditions including conditions related to a hyperactive immune system, chronic inflammation, and autoimmune disorders. Inflammatory disorders include, for example, acne vulgaris; acute febrile neutrophilic dermatosis; acute respiratory distress syndrome; Addison's disease; adrenocortical insufficiency; adrenogenital ayndrome; allergic conjunctivitis; allergic rhinitis; allergic intraocular inflammatory diseases, ANCA-associated small-vessel vasculitis; angioedema; ankylosing spondylitis; aphthous stomatitis; arthritis, asthma; atherosclerosis; atopic dermatitis; autoimmune disease; autoimmune hemolytic anemia; autoimmune hepatitis; Behcet's disease; Bell's palsy; berylliosis; balanitis circumscripta plasmacellularis; balanoposthitis; bronchial asthma; bullous herpetiformis dermatitis; bullous pemphigoid; carditis; celiac disease; cerebral ischaemia; chronic obstructive pulmonary disease; cirrhosis; Cogan's syndrome; contact dermatitis; COPD; Crohn's disease; Cushing's syndrome; dermatomyositis; diabetes mellitus; discoid lupus erythematosus; eczema (e.g., asteatotic eczema, dyshidrotic eczema, vesicular palmoplantar eczema); eosinophilic fasciitis; epicondylitis; erythema annulare centrifugum; erythema dyschromicum perstans; erythema multiforme; erythema nodosum; exfoliative dermatitis; fibromyalgia; focal glomerulosclerosis; giant cell arteritis; gout; gouty arthritis; graftversus-host disease; granuloma annulare; hand eczema; Henoch-Schonlein purpura; herpes gestationis; hirsutism; hypersensitivity drug reactions; idiopathic cerato-scleritis; idiopathic pulmonary fibrosis; idiopathic thrombocytopenic purpura; inflamed prostate; inflammatory bowel or gastrointestinal disorders, inflammatory dermatoses; juvenile rheumatoid arthritis; laryngeal edema; lichen nitidus; lichen planus; lichen sclerosus et atrophicus; lichen simplex chronicus; lichen spinulosus; Loeffler's syndrome; lupus nephritis; lupus vulgaris; lymphomatous tracheobronchitis; macular edema; multiple sclerosis; musculoskeletal and connective tissue disorder; myasthenia gravis; myositis; nummular dermatitis; obstructive pulmonary disease; ocular inflammation; organ transplant rejection; osteoarthritis; pancreatitis; pemphigoid gestationis; pemphigus vulgaris; polyarteritis nodosa; polymyalgia rheumatica; primary adrenocortical insufficiency; primary billiary cirrhosis; pruritus scroti; pruritic/inflammation, psoriasis; psoriatic arthritis; Reiter's disease; relapsing polychondritis; pyoderma gangrenosum; rheumatic carditis; rheumatic fever; rheumatoid arthritis; rosacea caused by sarcoidosis; rosacea caused by scleroderma; rosacea caused by Sweet's syndrome; rosacea caused by systemic lupus erythematosus; rosacea caused by urticaria; rosacea caused by zoster-associated pain; sarcoidosis; scleroderma; segmental glomerulosclerosis; septic shock syndrome; serum sickness; shoulder tendinitis or bursitis; Sjogren's syndrome; Still's disease; stroke-induced brain cell death; Sweet's disease; systemic dermatomyositis; systemic lupus erythematosus; systemic sclerosis; Takayasu's arteritis; temporal arteritis; thyroiditis; toxic epidermal necrolysis; tuberculosis; type-1 diabetes; ulcerative colitis; uveitis; vasculitis; and Wegener's granulomatosis.

The term "substantially pure," when referring to a protein or other derivative of the phyto-percolate, means the state of a substance that has been separated from the other components of the phyto-percolate. Typically, a substantially pure derivative is at least 80%, by weight, free from the other proteins and other molecules of the phyto-percolate. Preferably, the substantially pure derivative is at least 90%, 95%, or 99%, by weight, free from those organic molecules. A substantially pure protein derivative may be obtained, for example, by extracting it from a source other than the phyto-percolate. A protein derivative, for example, may be recombinantly expressed in another microorganism or in a cell-free translation system.

BRIEF DESCRIPTION OF THE DRAWINGS

The foregoing and other features and advantages of the present invention will be more fully understood from the following detailed description of illustrative embodiments, taken in conjunction with the accompanying drawing in which.

DETAILED DESCRIPTION

Figure 1:
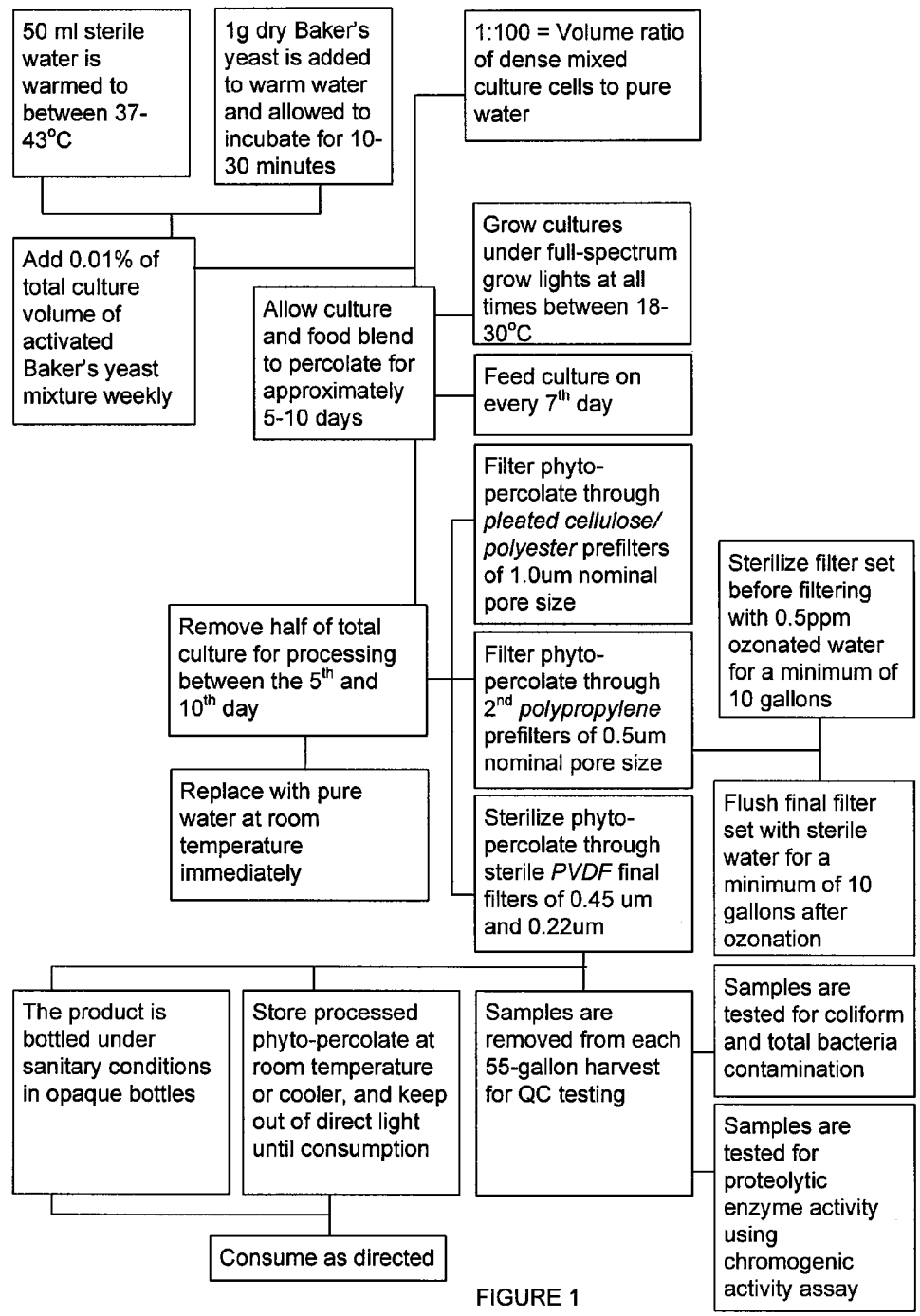
FIG. 1 is a flow chart showing a method of preparing a phyto-percolate.

The present invention provides a phyto-percolate that has therapeutic and other beneficial properties when administered to humans and other animals. Without being bound by any theory, it is believed that at least one of the therapeutically active agents in the phyto-percolate is an enzyme. Methods for preparing the phyto-percolate are also provided. Detailed embodiments of the present invention are disclosed herein, however, it is to be understood that the disclosed embodiments are merely exemplary of the invention, which may be embodied in various forms. Therefore, specific functional details disclosed herein are not to be interpreted as limiting, but merely as a basis for the claims and as a representative basis for teaching one skilled in the art to variously employ the present invention in virtually any appropriately detailed embodiment.

Phyto-Percolate Production

According to the invention, a phyto-percolate is derived from a culture comprised of freshwater algae, moss, bacteria, actinomycetes, and fungi. It is believed that the culture is comprised of at least one or more of the following genera:

| | | |
|---|---|---|
| Acinetobacter | Liefsonia | Staphylococcus |
| Aerococcus | Micrococcus | Stenotrophomonas |
| Aquaspirillium | Oedocladium | Stichococcus |
| Bacillus | Phyllobacterium | Streptomyces |
| Brevibacterium | Pseudomonas | Ulothrix |
| Caseobacter | Ralstonia | Variovorax |
| Chlorella | Rhizobium | Weeksella |
| Clavibacter | Rhodococcus | Xanthomonas |
| Corynebacterium | Riemerella | |
| Dermacoccus | Shingomonas | |

Particular note is made of the genera *Aquaspirillum, Bacillus, Pseudomonas, Ralstonia, Stenotrophomonas, Stichococcus*, and *Ulothrx*. Without being bound by any theory, it is believed that these genera are the most abundant organism in each culture and may be the primary producers of the phyto-percolate derivatives. A deposit of a culture resulting in a phyto-percolate of the present invention has been placed in the American Type Culture Collection, of Manassas, Va., as Deposit #: PTA-5863. This deposit is available to public upon grant of a patent disclosing the same. This deposit was made pursuant to 37 C.F.R. §1.808 and MPEP §2410.01 and therefore, access to the deposit will be available during pendency of this application making reference to the deposit to one determine by the Commissioner to be entitled thereto under 37 C.F.R. §1.14 and 35 U.S.C. 122 and with one exception, that all restrictions imposed by the depositor on the availability of to the public of the deposited biological material be irrevocably removed upon the granting of the patent.

In particular embodiments, a heterotrophic rotifer species exists in the cultures, as well as bacteria that have been identified as *Stenotrophomonas maltophilia, Ralstonia pickettii, Ralstonia paucula, Acinetobacter genospecies* 11, *Acinetobacter junii, Leifsonia aquatica, Riemerella anatipestifer, Variovorax paradoxes*, and *Streptomyces griseorubens*. Without being bound to any particular theory, it is believed that these species may produce compounds that are contributors to the effectiveness of the phyto-percolate.

A method of producing phyto-percolate is depicted in FIG. 1. Phyto-percolate cultures of approximately 100-200 ml of dense algal cells in approximately 2.5 gal, or approximately 10 liters, of reverse-osmosis purified sterile water are fed about 1 milliliter (ml) per week of liquid extract of live active yeast, or Baker's yeast, *Saccharomyces cerevisiae*, which has been prepared from 1.0 g dry active yeast added to 50 ml warm water, at between about 37° and about 43° C. The mixture is allowed to incubate for 10-30 minutes, or until it slightly foams. The cultures are fed in either 1.0 ml weekly doses, or 0.5 ml twice-weekly doses. It is contemplated within the scope of the invention that other yeast cultures may be used. It is further contemplated that other organic nutrients or substrates known in the art may be used such as glucose or proteose, or other algal growth media prepared from inorganic nutrients, supplements, and/or vitamins.

In one embodiment, the cultures are grown under full-spectrum grow lights at about 25° C., and produce a final unadjusted pH of between about 6.2 to about 7 that fluctuates. The cultures are grown in clear glass fishbowl containers having a volume of approximately 2.5 gal with semi-transparent plastic lids, with the exception of about a 3 mm hole in the lid for gas exchange. It is contemplated within the scope of the invention that other culture containers, ingredients, conditions and methods known in the art may be used that allow the cells to grow in a manner in which the phyto-percolate derivatives are expressed. Such methods may include larger batch, semi-continuous, continuous or other type culture systems including bireactors or photoreactors, may or may not include aeration or agitation, may or may not include solid, liquid, semi-solid or other form of growth media or substrate, may or may not include the above particular conditions of temperature, contact time or area, or light intensity.

In this particular embodiment the cultures are harvested weekly or bi-weekly, between the $5^{th}$ and $10^{th}$ day after feeding, by drawing off the top 1.25 gal of phytopercolate from each 2.5 gal culture. This is referred to as the "raw phyto-percolate." The algal or other cells and yeast food forming the phyto-percolate culture remain in the bottom of the culture container substantially undisturbed while the phyto-percolate is decanted. The decanted material is then processed as desired. The volume of the container is then optionally returned to original volume. Conveniently this is accomplished with reverse osmosis purified water at approximately room temperature, about 25° C. It is contemplated within the scope of the invention that other culture and harvest systems, timetables volumes and methods may be used that result in phyto-percolate derivatives.

Without being bound by any particular theory, it is believed the patterns of harvest and feeding affect enzyme production. It is believed that more frequent smaller feedings such as 0.5 ml twice-weekly may stimulate greater enzyme production than single large amount feedings such as 2 ml bi-weekly, while discouraging contamination with undesirable bacteria and rotifer colonization. Since enzyme systems are highly dynamic and are directly affected by the immediate surroundings, the suggestion is supported that a food blend such as a liquid extract of active Baker's yeast increases the active proteolytic enzymes in the phyto-percolate culture compared with other foods or nutrient blends.

The peaks of enzyme concentration in the percolate over the course of several weeks are mapped under various feeding regimens, and serve to dictate the optimal date for harvests. According to the invention, the enzyme concentration is analyzed in the cultures and processed phyto-percolate to detect any negative effects of regular harvesting on the algal cultures over time, and is combined with data on the effects of environmental and stress factors such as dark/light, starvation, and/or changes in temperature or pH, which may stimulate or discourage enzyme production. Methods for analyzing these parameters include the isolation and homogenization of select cultures to eliminate all variables besides those being tested, and include monitoring of chlorophyll, total protein and enzyme activity, utilizing spectro-photometric methods, to measure the health and enzyme activity of the cultures over the course of an isolated-variable experiment.

In this particular embodiment the method for analyzing proteolytic activity is a typical chromogenic assay using Chromogenix substrate from DiaPharma, S-2251: chromogenic substrate for plasmin and streptokinase-activated plasminogen. Chromogenic substrates are peptides that react with proteolytic enzymes and proportionally change color as the substrate is lysed by the enzymes. The color change may be measured spectrophotometrically over time and is proportional to the proteolytic activity. The synthetic chromogenic assay substrates are designed to have enzyme binding selectivity similar to that of the enzyme's natural substrate. It is believed that the enzymes present in phyto percolate are selective for substrates including fractionated proteins and fibrin. It is contemplated within the scope of the invention that other methods for analyzing proteolytic activity and phyto-percolate derivatives may be used.

Enzyme activity for samples of described phyto-percolate currently ranges from 15-50 mU/mL of plasmin-like activity, when phyto-percolate is prepared as described. These values have been found to correlate with clinical observations of reduced pathological fibrin in humans orally consuming phyto-percolate. Methods for evaluating in vivo effects of phyto-percolate include peripheral blood observations on wet and dry blood smears, diagnostic and/or analytical blood tests, and various clinical observations and measurements such as body weight. Reductions in excess pathological fibrin and platelet aggregation have been observed, which are secondary to inflammation and tissue destruction. Changes in white blood cell mobility and number have also been observed. Anti-inflammatory effects of phyto-percolate in vivo have also been monitored with independent blood laboratory studies focusing on chronic inflammatory activity and hyper-coagulant states.

In an alternative embodiment, the phyto-percolate may be produced using a continuous culture format in which the phyto-percolate is substantially continuously removed from the culture and the lost volume is replaced with fresh culture media and/or nutrients. Further, the phyto-percolate may be produced using a bioreactor that is suitable for production on a larger scale than the batch culture method described above.

Phyto-Percolate Filtration

After harvest of the phyto-percolate from the cultures, the decanted fluid is filtered through a series of depth prefilters and sterile membrane filters made of low-protein binding materials. Examples of suitable final sterilizing filters are provided by Millipore Corp. Durapore brand filters, made of PVDF material. These have been shown to protect the enzyme concentration, and provide a final sterile filtration level of about 0.22 microns, as well as being chemically inert to ozonated water. Ozonated water is used for sterilizing the filter system, as it does not leave a damaging residue like chlorine.

All filters are 10" cartridge membrane or depth filters of various chemically-inert materials. The prefilters are housed in cartridge filter housings made of styrene-acrylonitrile (SAN). The final filters are housed in polypropylene (PP) housings with Kynar fittings. The material is harvested and filtered using Tygon tubing, peristaltic pumps and 55 gallon containers or other containers that have been pre-sterilized with ozonated water.

The phyto-percolate passes through a filtration regimen comprised of two pre-filters in SAN housings of pore size 1 μm (nominal), made of pleated cellulose/polyester. Examples of these filters are manufactured by Cole-Parmer, Vernon Hills, Ill., USA, catalog number EW-29830-20. It is contemplated within the scope of the invention that other filters know in the art may be used in this step as pre-filters, that are chemically inert.

The phyto-percolate is again filtered using a second stage pre-filter made of polypropylene in a polypropylene housing, with a nominal pore size of about 0.5 um. In one illustrative embodiment, this finishing filter is manufactured by Millipore Corporation, Bedford, Mass., Durapore® brand, Catalog # D00501S01. It is contemplated within the scope of the invention that other filters known in the art may be used in this step as second pre-filters, that are chemically inert.

The phyto-percolate is then passed through a pre-sterilized final filter that sterile-filters the phyto-percolate and removes all traces of bacteria, yeast, mold, algae and other particle contaminants. According to the invention, a final filter set consists of sterile membrane filters in PP housing having progressively smaller pore sizes of 0.45 um and 0.2211μ (absolute). These finishing filters' membranes are made of hydrophilic extremely-low protein-binding PVDF. In one illustrative embodiment, these finishing filters are manufactured by Millipore Corporation, Durapore® brand, Catalog #'s CVHIO1TPE and CVDIO1TPE. It is contemplated within the scope of the invention that other filters know in the art may be used that are inert to the phyto-percolate derivatives and processing and sanitizing materials including ozonated water. It is also contemplated within the scope of the invention that other methods of processing may be used.

Filtration by size exclusion removes approximately >99.9% of contaminants such as bacteria, yeast and mold spores, and algal cells. It is also believed to preserve enzymatic activity if filter materials are made of low-protein-binding, chemically-inert materials. The resulting liquid, the phyto-percolate, is substantially comprised of water, active enzymes, proteins and sugars. The phyto-percolate, after passing through the finishing filter is then usefully stored in sealed sterile 55 gal HDPE drums at between 21° and 27° C. until bottling. Samples are taken from each batch immediately after filtering to test for enzyme efficacy and contamination and for standardization. It is contemplated within the scope of the invention that other methods of sampling and testing may be used. The acceptable values for fibrinolytic enzyme efficacy to be administered p.o. are observed in the phyto-percolate as between 0 and 50 milli-units of plasmin-like activity; however higher levels may provide greater therapeutic benefit. It is believed that this filtered phyto-percolate contains approximately 50 ppm of the 67.5 kDa protein (see below).

The phyto-percolate is processed and bottled under sanitary conditions known in the art using ozone sterilization. It is believed that this step avoids enzyme degradation associated with the use of chlorine or heat sterilization because ozone leaves no residue if left to dissipate, or if followed by a rinse of sterile water. It is contemplated within the scope of the invention that other methods of filtration and sanitization known in the art may be used that are not unreasonably degrading of the enzymatic or other activity. The phytopercolate is usefully packaged in opaque UV-protectant bottles and shipped with cold packs to reduce product degradation. It is contemplated within the scope of the invention that other methods of packing, bottling, storing, and transporting may be used.

Phyto-Percolate Characterization

It is believed that the raw phyto-percolate, prior to filtration, is a complex mixture of macromolecules. It was expected that the filtration process described above reduced the molecular complexity of the phyto-percolate filtrate. We performed several physico-chemical tests to determine the composition of the filtrate. In each case, the phyto-percolate filtrate was lyophilized, redissolved in ddH$_2$0, and refiltered to remove any undissolved particulate matter.

Figure 2:
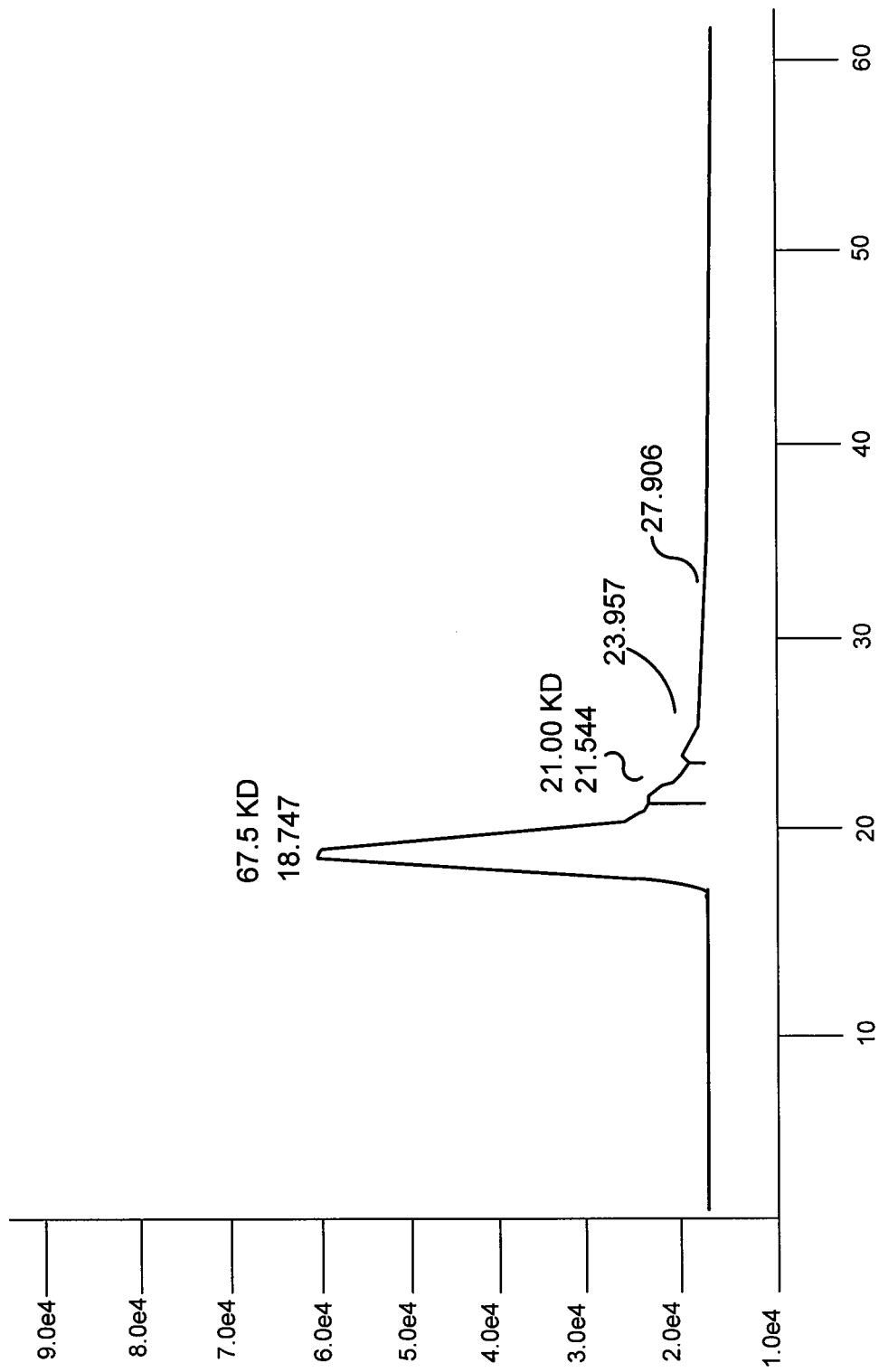
FIG. 2 is an FIPLC chromatogram of the diluted phyto-percolate.

A sample of the lyophilized phyto-percolate was subjected to isocratic reverse phase HPLC, on a size-exclusion chromatography column (TSK-GEL Super SW Series; Tosoh Biosciences, Montgomeryville, Pa.), under non-denaturing conditions. Proteins were identified using a micro flow cell UV detector at 280 nm. As shown in FIG. 2, a major protein species of 67.5 kDa was identified (retention time 18.747 minutes). The 67.5 kDa peak contributed about 90% of the total signal measured at 280 nm. Also detected were peaks at retention times of 21.544 minutes (21.0 kDa) and 23.957 minutes. Analysis under denaturing and other conditions indicates that the 21.0 kDa species is a protein molecule and the 23.957 minute peak is primarily polysaccharide. The major components of the phyto-percolate (the 67.5 kDa protein, 21.0 kDa protein, and the polysaccharide identified at 23.957 minutes) are referred to herein as phyto-percolate derivatives and may contribute to the biological and therapeutic efficacy of the phyto-percolate.

Figure 3:
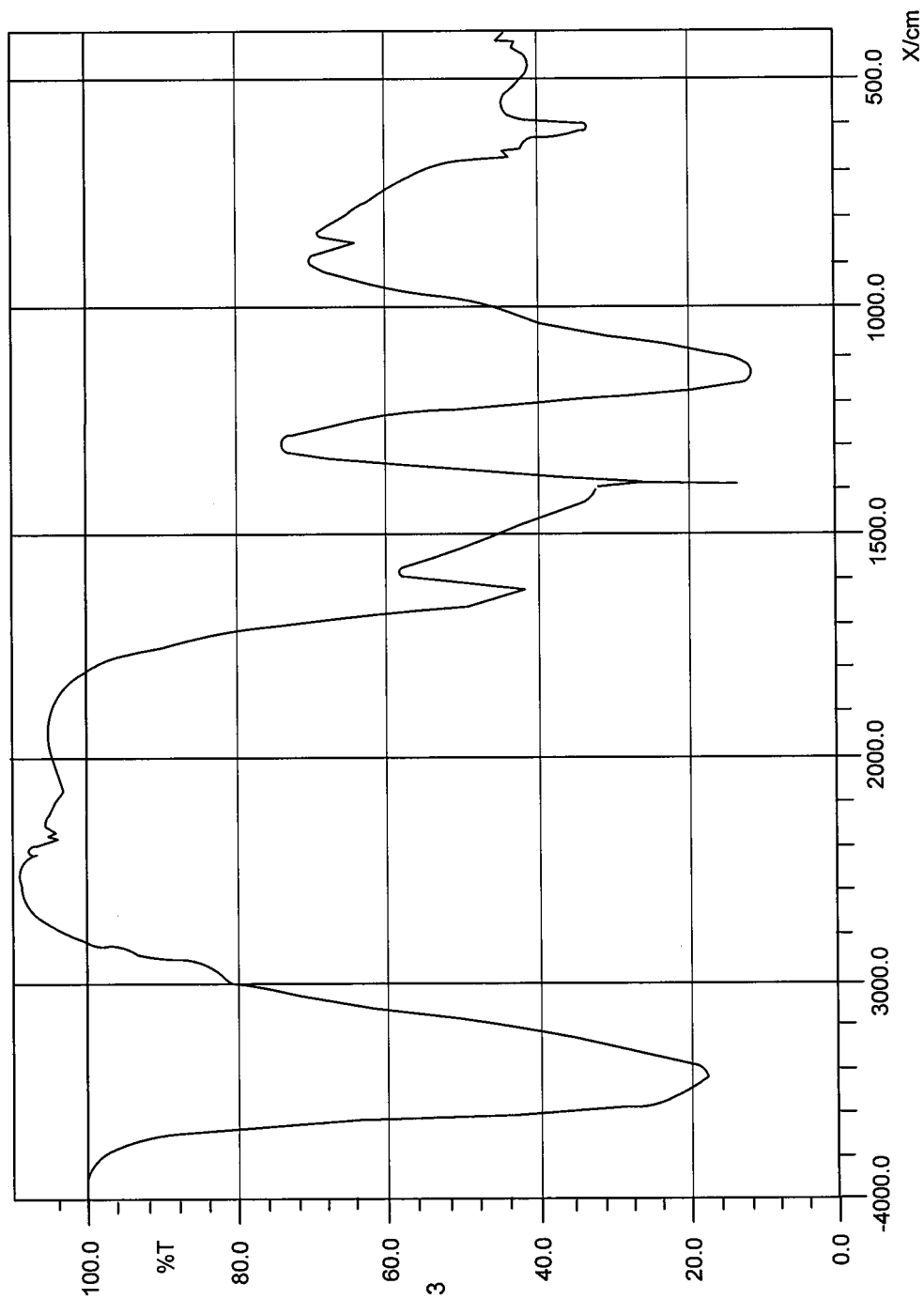
FIG. 3 is an FTIR spectrum of the diluted phyto-percolate.

Another sample of the lyophilized phyto-percolate was subjected to Fourier Transform Infrared (FTIR) spectroscopy. The results are provided in FIG. 3. FIG. 3 shows a spectrum that is characteristic of a dissolved protein sample.

Figure 4:
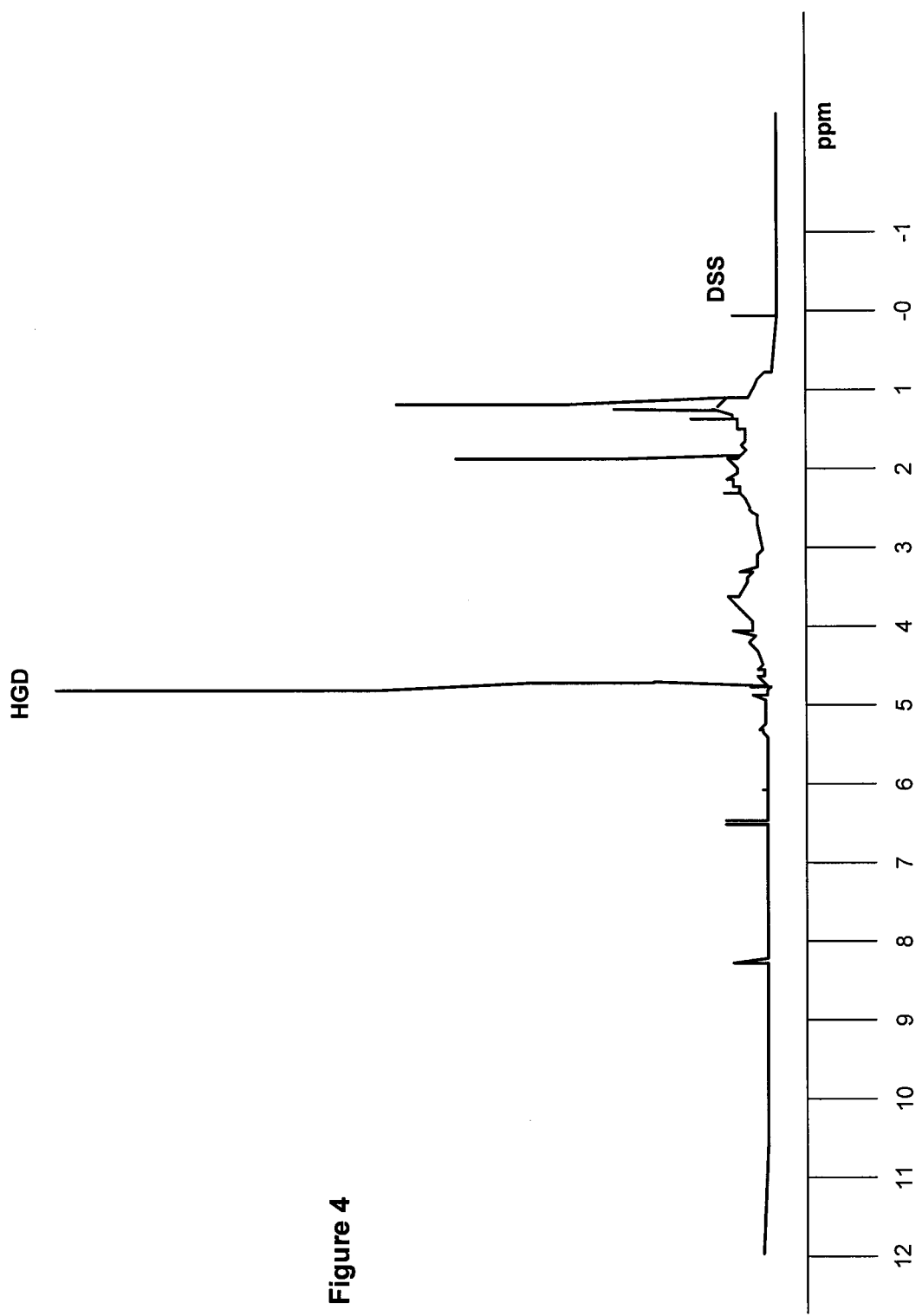
FIG. 4 is a [$^1$H]-NMR spectrum of the diluted phyto-percolate.

A third sample of the lyophilized phyto-percolate was used for [$^1$H]-NMR. The NMR spectrum is provided in FIG. 4. Here again, the results are consistent with a single protein species.

Weight Management Using Phyto-Percolate

Excessive weight has emerged as a prominent and growing health problem. Greater than 61% of Americans over the age of 20 are overweight, 25% of whom are obese. Second only to tobacco use as the top underlying preventable cause of death, excessive weight is a major risk factor for developing diabetes, heart disease, hypertension, gallbladder disease, arthritis, lung diseases, and certain types of cancer.

EXAMPLE 1

Rodent Model of Weight Loss

A 21 day weight loss study using twelve mature (12 month old) Sprague-Dawley rats was performed. Each animal was orally administered 10 ml/kg of undiluted and unfiltered phyto-percolate (i.e., raw phyto-percolate) for 14 days, followed by non-dosing for 7 days. Each animal was weighted daily and observed for signs of toxicity. As shown in more detail in Table 1, the rats lost an average of 33 grams (6.3%) of body weight over the initial 14 day dosing period. They immediately began to regain lost body weight upon cessation of phyto-percolate administration. By the 21 day time point (7 days of non-dosing), the rats had lost an average of 25 grams (4.7%) of initial body weight (i.e., gained an average of 8 grams since phyto-percolate cessation).

The test animals were observed for adverse reactions immediately after each dose and at 4 and 24 hours subsequent. Daily observation for adverse reactions was continued during the 7 day non-dosing period. Specifically, clinical observations for adverse reactions were made for respiration, motor activity, convulsions, reflexes, ocular signs, salivation, piloerection, analgesia, muscle tone, gastrointestinal effects, and skin/dermal alterations. Gastrointestinal effects were the only observed adverse reaction. Soft to loose stool was observed in all test animals. No other adverse reaction was observed.

EXAMPLE 2

Human Weight Loss and Glucose Control Study

TABLE 1

Individual Weight Loss Data

| Test Subject | Pre-dosing Weight (g) | 14 Day Weight (g) | Weight Loss (% Initial Body Weight) | 21 Day Weight (g) | Weight Loss (% Initial Body Weight) |
|---|---|---|---|---|---|
| 1 | 484 | 443 | 41 (8.5%) | 453 | 31 (6.4%) |
| 2 | 482 | 461 | 21 (4.4%) | 479 | 3 (0.6%) |
| 3 | 549 | 521 | 28 (5.1%) | 531 | 18 (3.3%) |
| 4 | 536 | 499 | 37 (6.9%) | 507 | 29 (5.4%) |
| 5 | 510 | 462 | 48 (9.4%) | 468 | 42 (8.2%) |

TABLE 1-continued

Individual Weight Loss Data

| Test Subject | Pre-dosing Weight (g) | 14 Day Weight (g) | Weight Loss (% Initial Body Weight) | 21 Day Weight (g) | Weight Loss (% Initial Body Weight) |
|---|---|---|---|---|---|
| 6 | 488 | 459 | 29 (5.9%) | 465 | 23 (4.7%) |
| 7 | 535 | 506 | 29 (5.4%) | 514 | 21 (3.9%) |
| 8 | 586 | 558 | 28 (4.8%) | 562 | 24 (4.1%) |
| 9 | 569 | 504 | 65 (11.4%) | 518 | 51 (9.0%) |
| 10 | 522 | 492 | 30 (5.7%) | 498 | 24 (4.6%) |
| 11 | 556 | 532 | 24 (4.3%) | 537 | 19 (3.4%) |
| 12 | 524 | 503 | 21 (4.0%) | 507 | 17 (3.2%) |
| AVG | 528.4 | 495.0 | 33.4 (6.3%) | 503.3 | 25.1 (4.7%) |

A single-center, prospective, randomized, triple-masked, placebo-controlled parallel-group-design pilot clinical trial of the phyto-percolate was performed using two different batches of the phyto-percolate. This trial was conducted in accordance with FDA regulations and under a protocol approved by an Institutional Review Board (IRB).

Subjects: Primary inclusion criteria were men and women having a body mass index (BMI) of 25-40 m/kg$^2$, 18-70 years old (inclusive), and desirous of losing weight. Major exclusion criteria were moderate to severe co-morbid disease (e.g., cancer); history of stroke, transient ischemic attack (TIA), or similar conditions; uncontrolled hypertension, insulin-dependent diabetes, renal disease, moderately severe cardiac disease, lupus, alcohol abuse, and current or recent use of certain medications including medications and/or supplements for weight loss, glucose management, or arthritis. Women were excluded if they were pregnant, nursing, or actively trying to become pregnant.

Protocol: Patients were assigned to self-administer one ounce of filtered phyto-percolate or placebo three times each day (t.i.d.) on an empty stomach at least 30 minutes before a meal. Subjects were asked to participate in a reduced carbohydrate diet and light exercise program and complete a one-day-per-week Food Log and a daily Exercise Log for the duration of the clinical trial. Patients were evaluated during a baseline examination and then again at 2-week, 4-week, and 6-week visits. Evaluations included measurement of body weight, arm and waist circumference, and body fat measurements.

Glucose Control Study: At the baseline examination and at the 4-week and 6-week visits, patients' fasting (12 hour) blood glucose was measured and then their blood glucose was measured one hour after a glucose challenge (25 grams of jelly beans; 90.4% carbohydrate). The difference between the glucose challenge reading and the baseline reading in a single visit is an indicator of the patient's ability to regulate serum glucose levels.

Test Materials: The patients in the treatment groups were assigned one of two different lots (Batch 1 and Batch 2) of phyto-percolate prepared as described above. The placebo product was similar in appearance (color, viscosity, and odor) to the diluted phytopercolate. All test materials were dispensed in unlabeled blue bottles with instructions to refrigerate after opening.

Enrollment: A total of 44 subjects were enrolled and randomized for this trial. Ten subjects completed the study on Batch 1 (Cohort 1) of the phyto-percolate and twelve subjects completed Batch 2 (Cohort 2). Seven subjects completed the placebo phase of the trial.

Results: There were no significant adverse events reported. Patients in the treatment arms of the study reported greater energy and reduced hunger compared to the Placebo group. The remaining results are as follows:

After 2, 4, and 6 weeks of treatment with the diluted filtered phyto-percolate, the average percent total weight loss (above placebo) for all treated patients (Cohorts 1 and 2; n=22) 77.7%, 48.5%, and 68.1%, respectively. After six weeks of phyto-percolate treatment, Cohort 1 lost an average of 106% (9.03 lbs) and Cohort 2 lost an average of 37% (6.01 lbs) more than the weight loss measured in the Placebo group (4.39 lbs).

TABLE 2

Average Weight Loss

|  | 2-Week | 4-Week | 6-Week |
|---|---|---|---|
| Placebo (n = 7) | 2.60 | 3.71 | 4.39 |
| Cohort 1 (n = 10) | 5.71 | 6.81 | 9.03* |
| Cohort 2 (n = 2) | 3.71 | 4.43 | 6.01 |

*p < 0.10 (unpaired Student's t-test)

TABLE 3

Frequency Distribution of Weight Loss in Individual Patients at 6 Weeks

| Weight Loss | Placebo (number of patients) | Cohort 1 (number of patients) |
|---|---|---|
| >+1 lb. | — | 1 |
| +1 lb. > patient > 1 lb. | — | 1 |
| −1 lb. > patient > −3 lb. | 2 | — |
| −3 lb. > patient > −5 lb. | 2 | — |
| −5 lb. > patient > −7 lb. | 3 | 1 |
| −7 lb. > patient > −9 lb. | — | 3 |
| −9 lb. > patient > −11 lb. | — | 2 |
| −11 lb. > patient > −13 lb. | — | — |
| −13 lb. > patient > −15 lb. | — | — |
| −15 lb. > patient > −17 lb. | — | 1 |
| −17 lb. > patient > −19 lb. | — | — |
| <−19 lb. | — | 1* |

*maximum weight loss was 28 lbs.

TABLE 4

Arm and Waist Circumference-
Difference Between Baseline and 6 Weeks

|  | Placebo | Cohort 1 | Cohort 2 |
|---|---|---|---|
| Arm | 0.083" | 0.41" * | 0.13" |
| Waist | 1.09" | 2.08"** | 1.34" |

* p < 0.042
** p < 0.21

TABLE 5

Body Composition-Percent Body Fat:
Difference Between Baseline and 6 Weeks

|  | Placebo | Cohort 1 | Cohort 2 |
|---|---|---|---|
| Body Fat @ Baseline | 39.1% | 39.2% | 39.0% |
| Improvement in Body Fat (lbs) | 2.11 | 6.03* | 2.89 |
| Improvement in Lean Mass (lbs) | 0.16 | 0.79** | 0.24 |

*p < 0.01
**p < 0.15

TABLE 6

Frequency Distribution of Body Fat Loss in Individual Patients at 6 Weeks

| Weight Loss | Placebo (number of patients) | Cohort 1 (number of patients) |
|---|---|---|
| >+1 lb. | — | 2 |
| +1 lb. > patient > −1 lb. | 2 | 1 |
| −1 lb. > patient > −3 lb. | 2 | — |
| −3 lb. > patient > −5 lb. | 2 | 2 |
| −5 lb. > patient > −7 lb. | 1 | 2 |
| −7 lb. > patient > −9 lb. | — | — |
| −9 lb. > patient > −11 lb. | — | 1 |
| −11 lb. > patient > −13 lb. | — | — |
| −13 lb. > patient > −15 lb. | — | — |
| −15 lb. > patient > −17 lb. | — | 1 |
| −17 lb. > patient > −19 lb. | — | — |
| <−19 lb. | — | 1 |

* maximum weight loss was 28 lbs.

TABLE 7

Serum Glucose Levels In Individual Patients In Cohort 1 (mg/dl)

| Patient | Baseline | | | 4-Week | | | 6-Week | | |
|---|---|---|---|---|---|---|---|---|---|
| | Fast | Chal. | Diff. | Fast | Chal. | Diff. | Fast | Chal. | Diff. |
| 1 | 158 | 264 | 106 | 155 | 246 | 91 | 152 | 238 | 86 |
| 2 | 72 | 128 | 56 | 89 | 107 | 18 | 80 | 94 | 14 |
| 3 | 75 | 135 | 60 | 87 | 130 | 43 | 91 | 117 | 26 |
| 4 | 73 | 128 | 55 | 78 | 74 | −4 | 76 | 80 | 4 |
| 5 | 105 | 151 | 46 | 104 | 127 | 23 | 103 | 125 | 22 |
| 6 | 139 | 210 | 71 | 129 | 198 | 69 | 126 | 181 | 55 |
| 7 | 145 | 204 | 59 | 124 | 200 | 76 | 132 | 195 | 63 |
| 8 | 85 | 122 | 37 | 74 | 159 | 85 | 83 | 133 | 50 |
| 9 | 91 | 143 | 52 | 91 | 125 | 34 | 92 | 121 | 29 |
| 10 | 78 | 119 | 41 | 92 | 99 | 7 | 88 | 98 | 10 |
| Mean | | | 58.3 | | | 44.2 | | | 35.9 |
| n > 126* | 3 | | | 2 | | | 2 | | |

TABLE 8

Group Mean Data For Glucose Tolerance Test (mg/di)

| | Baseline | 4-Week | 6-Week |
|---|---|---|---|
| Placebo | 61.7 | 58.3 | 54.0 |
| Improvement | | 3.4 (5.5%) | 7.7 (12.3%) |
| Cohort 1 | 58.3 | 44.2 | 35.9 |
| Improvement | | 14.1 (24.2%) | 22.4 (39.6%)* |
| Cohort 2 | 60.6 | 56.2 | 55.4 |
| Improvement | | 4.2 (6.9%) | 5.2 (8.6%) |

*values > 126 mg/dl are indicative of diabetes.
*p < 0.08

Conclusions: The weight loss, improvement in body fat, improvement in glucose control, as well as energy and hunger categories over the course of this six-week study for those on the phyto-percolate was strong, particularly when compared to the placebo group.

Cohort 1 lost about twice as much weight (1.5 lbs/week) as the placebo group (0.78 lbs/week). Seven of the ten subjects in Cohort 1 lost seven pounds or more, while none of the seven in the placebo group lost that much weight. Correspondingly, a significant reduction in waist size was measured in Cohort 1.

Significant improvements also were measured in the glucose tolerance test. Test subjects demonstrated an average of 2.6× (156%) and 1.7× (69%) improved glucose control at 4 weeks and 6 weeks, respectively, when compared to the placebo group. Furthermore, 6 of the 22 test subjects met the clinically important criterion of >50% control over baseline. Three of these six demonstrated complete control of the glucose challenge, defined as >85% glucose control over baseline.

In Vitro Anti-inflammatory Effects: COX-2 Inhibition

Cyclooxygenase-2 (COX-2) is a key regulator of the inflammatory cascade. COX-2 inhibitors are believed to reduce inflammation by blocking prostaglandin production. In view of the adverse effects associated with mixed COX inhibitors (aspirin, ibuprofen, and naproxen) and the presently available COX-2-specific inhibitors (valdecoxib, celecoxib, rofecoxib), there is a need for improved anti-inflammatory therapies with fewer side effects.

Three separate preparations of the phyto-percolate were screened, using an in vitro assay, for COX-2 inhibition. Riendeau et al., *Can. J. Physiol. Pharmacol.* 75: 1088-1095, 1997; Warner et al., *Proc. Natl. Acad. Sci. USA* 96: 7563-7568, 1999. Briefly, this assay measured to conversion of 0.3 µM arachidonic acid to $PGE_2$ by human recombinant insect Sf21 cells expression human COX-2. The incubation buffer contained 100 mM Tris-HCl (pH 7.7), 1 mM glutathione, 1 µM hematin, and 500 µM phenol. $PGE_2$ was quantified using an enzyme-linked immunoassay (EIA).

Sample 1 was a sample of diluted phyto-percolate concentrated approximately 100-fold by drying under $N_2$. Sample 2 was prepared by drying a 4800 µl sample of diluted phyto-percolate under $N_2$ and reconstituting it in 96 µl of dd$H_2O$ just prior to assay. Sample 3 was prepared by lyophilizing a 4800 µl sample of diluted phyto-percolate and reconstituting it in 96 µl of dd$H_2O$ just prior to assay. The concentrations of phyto-percolate used, 100×, 10×, and l×, refer to 10 µl, 1 µl, and 0.1 µl of sample, respectively, in a final assay volume of 100 µl. Rofecoxib was used as a positive control for COX-2 inhibition. Each sample was assayed in at least three concentrations and the assays were performed in duplicate.

TABLE 9

COX-2 Inhibition By Phyto-percolate

| Sample | Centration | % COX-2 Inhibition (Individual assay values) | $IC_{50}$ |
|---|---|---|---|
| 1 | 100X | 29 (27, 30.9) | >100X |
| | 10X | 11 (9.2, 13.4) | |
| | 1X | −4 (−9.0, 0.3) | |
| 2 | 100X | 61 (66.7, 56.1) | 46.5X |
| | 10X | 27 (23.7, 30.5) | |
| | 1X | 20 (13.3, 27.6) | |
| 3 | 100X | 58 (63.9, 52.3) | 61.9X |
| | 10X | 24 (21.7, 26.0) | |
| | 1X | 18 (13.3, 23.1) | |
| rofecoxib | 1 µM | 88 (90.1, 85.6) | 0.198 µM |
| | 0.3 µM | 55 (58.8, 51.8) | |
| | 0.1 µM | 33 (34.7, 31.5) | |
| | 0.03 µM | 16 (22, 10.5) | |
| | 0.01 µM | 11 (8.2, 14) | |

In Vivo Anti-inflammatory Effects: Carageenan-Induced Paw Edema

The carrageenan-induced paw edema assay was used as an in vivo indicator of the anti-inflammatory effects of the phyto-percolate. Carrageenan induces local inflammation and edema when injected into the paw pad of a rat (Di Rosa et al., 1971). The development of paw edema is believed to be biphasic (Vinegar et al., 1969). The initial phase is attributable to the local release of histamine and serotonin (Crunkhon et al., 1971) and the second phase is caused by prostaglandin release as a result of COX activation. The second phase is measured as an increase in paw volume and has been demonstrated to be responsive to steroidal and non-steroidal anti-inflammatory agents.

Groups of test subjects (n=6) received oral doses of either vehicle control (water; 5 ml/kg), indomethacin (30 mg/kg), aspirin (100 mg/kg), unfiltered phyto-percolate (10 ml/kg), or filtered phyto-percolate (10 ml/kg) 30 minutes prior to intraplantar administration of carrageenan (0.1 ml of a 1% solution). Paw volume was measured at 0, 2, 4, 6, 8, and 20 hours after treatment using a plesthysmometer to measure volume displacement. Each treatment group is compared to control.

As shown in Table 10, the paw volume of the control animals and all treatment groups nearly doubled in two hours and remained so through the four hour time point. By six hours, paw volume was reduced by 30% and 50% in the groups administered the filtered and unfiltered phyto-percolate, respectively. This reduction in edema was significantly better than that observed for either the indomethacin or the aspirin groups at this time. Further, the reduction in edema measured for the two phyto-percolate groups was comparable to both the indomethacin and aspirin groups at the 8 hour and 20 hour time points.

TABLE 10

In Vivo Anti-inflammatory Effects of Phyto-percolate
Mean paw volume (ml) ± SD (% change from control)

| Group | 0 hours | 2 hours | 4 hours | 6 hours | 8 hours | 20 hours |
|---|---|---|---|---|---|---|
| Control | 1.24 ± 0.17 | 2.18 ± 0.24 | 2.17 ± 0.27 | 2.12 ± 0.15 | 2.05 ± 0.08 | 1.85 ± 0.08 |
| Indomethacin | 1.25 ± 0.05 (1%) | 2.25 ± 0.23 (7%) | 2.18 ± 0.22 (1%) | 2.00 ± 0.22 (−12%) | 1.83 ± 0.23 (−22%) | 1.37 ± 0.10 (−38%) |
| Aspirin | 1.25 ± 0.08 (1%) | 2.22 ± 0.28 (4%) | 2.07 ± 0.23 (−10%) | 1.92 ± 0.18 (−20%) | 1.80 ± 0.18 (−25%) | 1.42 ± 0.16 (−23%) |
| Filtered | 1.22 ± 0.04 (−2%) | 2.15 ± 0.10 (−3%) | 2.15 ± 0.10 (−2%) | 1.78 ± 0.10 (−34%) | 1.78 ± 0.10 (−27%) | 1.35 ± 0.08 (−30%) |
| Unfiltered | 1.20t 0.13 (−4%) | 2.15 ± 0.12 (−3%) | 2.13 ± 0.10 (−4%) | 1.67 ± 0.10 (−45%) | 1.67 ± 0.10 (−38%) | 1.28 ± 0.12 (−37%) |

Immunological Effects: Rodent Model of HIV Infection

The effect of treatment using the phyto-percolate was investigated using a rat model of HIV infection. The HIV model used inoculates rats with seven (7) of the nine (9) HIV genes, making it a non-contagious model that develops full symptoms of HIV by 9 months after inoculation, with a life expectancy of 12 months.

Some of the most devastating symptoms of HIV manifest themselves in the liver and the immune system. Liver problems are frequent causes of illness and death in people with HIV infection. Throughout the study, liver function tests including AST, ALT, GGTP, bilirubin, and albumin were monitored in the treatment and control groups. C-reactive protein was assayed as an inflammatory marker. The immune response was monitored using IgG, IgA, and IgM levels which are known to decline during the progression of AIDS.

For testing, serum was drawn by cardiac puncture for baseline (pre-inoculation) values. The treatment group received diluted phyto-percolate for their drinking water, which was allowed ad libitum, while the control group received filtered water. Serum was drawn by cardiac puncture, as above, every thirty (30) days until the termination of the study.

After 60 days of treatment with the diluted phyto-percolate, the treatment group had an average 30% increase in IgA levels, 50% increase in IgG levels, and a 40% reduction in C-reactive protein (C-RP) levels, relative to the untreated group (Table 11). No significant differences in body weight, average daily food consumption, or average daily liquid consumption were detected between the groups

TABLE 11

Serum Analysis From Rat HIV Study

| Animal Group | AST (U/L) | ALT (U/L) | Bilirubin (mg/dL) | C-RP (mg/ml) | IgG (mg/dL) | IgM (mg/dL) | IgA (mg/dL) |
|---|---|---|---|---|---|---|---|
| Control | | | | | | | |
| Base | 117 | 70 | 0.07 | 3.41 | 57 | 27 | 18 |
| 1 Mo. | 95 | 60 | 0.12 | 0.65 | 69 | 26 | 24 |
| 2 Mo. | 122 | 67 | 0.12 | 0.93 | 120 | 26 | 24 |
| HIV | | | | | | | |
| Base | 116 | 77 | 0.07 | 3.37 | 60 | 26 | 21 |
| 1 Mo. | 166 | 76 | 0.21 | 0.58 | 108 | 27 | 25 |
| 2 Mo. | 139 | 81 | 0.13 | 0.56 | 167 | 23 | 38 |

Administration of Phyto-Percolate

The phyto-percolate dosage will vary with the severity of the disease, the biochemical activity of the disease, and the age and weight of the subject. The effects of using the phyto-percolate will be measured using standard parameters known in the art for any such disease state.

In one embodiment, the phyto-percolate is orally administered as a liquid. As described in several of the foregoing examples, the phyto-percolate is diluted in filtered water to about 50 ppm of the protein species of the 67.5 kDa peak measured by HPLC and UV detection (described above). However, depending upon the severity of disease or desired clinical outcome, the concentration of phyto-percolate (and hence the dosage for the protein species) may be altered. For example, the protein species may be present in the orally administered liquid in concentrations including about 100 ppm, 250 ppm, 500 ppm, 750 ppm, 1000 ppm, 1500 ppm, or more. It is also contemplated that the protein fraction is isolated from the phyto-percolate and formulated for parentera administration (e.g., intravenous, intramuscular, and subcutaneous injection, topical, rectal or vaginal administration or other).

In an adult subject, the dosage of diluted phyto-percolate will vary from about one ounce per day, generally on an empty stomach, such as for maintenance and the retardation of aging, to about an ounce every hour, up to about 12 ounces per day, in a hospitalized burn or accident case, or during the chemotherapy infusion. The controlled diabetic or cardiovascular subject is generally treated at about two to three ounces of phyto-percolate per day. Dosing on an empty stomach is noted because of the potential for interference on phyto-percolate function from food-stimulated gastrointestinal activities. A 50-70 lb. child is dosed at about three to four ounces per day, generally dosing on an empty stomach, during an acute infection. The greater the free radical oxidative tissue destructive activity caused by age or disease state, the greater the recommended dosage of the phyto-percolate. Without being bound to any particular theory, it is thought that the intake of phyto-percolate per day is more directly related to the severity of oxidative tissue destruction than to the weight of the subject.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto. Likewise it should be understood that the phyto-percolate can be used to enhance the well being and performance of animals.

The foregoing has been a description of an illustrative embodiment of the present invention. While several illustrative details have been set forth, such are only for the purpose of explaining the present invention. Various other changes, omissions and additions in the form and detail thereof may be made therein without departing from the spirit and scope of the invention.

What is claimed is:

1. A method of producing a phytopercolate having enzymatic activity comprising the steps of: (a) producing a phytopercolate culture from microorganisms of ATCC Deposit #PTA-5863 and purified water; (b) feeding said phytopercolate culture with a nutrient; and (c) decanting said phytopercolate from said phytopercolate culture.

2. The method of claim 1, wherein said phytopercolate culture comprises a mixture of approximately 100-200 mL of dense algal cells and approximately 10 Liters of purified water.

3. The method of claim 1, wherein said enzymatic activity ranges from 15-50 mU/mL.

4. The method of claim 1, wherein said phytopercolate is fed with nutrient sufficient liquid growth media.

5. The method of claim 1, wherein said feeding comprises 1 mL per week of live active yeast liquid extract prepared from 1.0 g dry active yeast and 50 mL warm water.

6. The method of claim 1, wherein said decanting occurs between the $5^{th}$ and $10^{th}$ day after said feeding.

7. The method of claim 1, further comprising a step of filtering said phytopercolate.

8. The method of claim 7, wherein said filtering comprises: a first stage of filtration through a filter having a 1 μm nominal pore size; a second stage of filtration through a filter having a 0.5 μm nominal pore size; and a final stage of filtration through sterile membrane filters having progressively smaller absolute pore sizes of 0.45 μm and 0.22 μm.

9. The method of claim 1, wherein said nutrient comprises a liquid extract of live *Saccharomyces cerevisiae*.

10. A method of treating inflammation in a mammal, said method comprising the step of administering to said mammal a therapeutically effective amount of the phytopercolate prepared by the method of claim 1 wherein said inflammation is treated.

11. The method of claim 10, wherein said mammal is a human, a dog, a cat, a cow, a pig, or a horse.

12. A method of treating obesity, diabetes, cancer, viral infections, oxidative stress, cardiovascular diseases, cerebral vascular diseases, immune system disorders, metabolic disorders, HIV, or gastric reflux disease in a mammal, said method comprising the step of administering to said mammal a therapeutically effective amount of the phytopercolate prepared by the method of claim 1 wherein said obesity, diabetes, cancer, viral infections, oxidative stress, cardiovascular diseases, cerebral vascular diseases, immune system disorders, metabolic disorders, HIV, or gastric reflux disease is treated.

13. The method of claim 12, wherein said mammal is a human, a dog, a cat, a cow, a pig, or a horse.

* * * * *